US009198752B2

(12) United States Patent
Woods

(10) Patent No.: US 9,198,752 B2
(45) Date of Patent: Dec. 1, 2015

(54) INTRAOCULAR LENS IMPLANT HAVING POSTERIOR BENDABLE OPTIC

(75) Inventor: Randall Woods, Gilbert, AZ (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1378 days.

(21) Appl. No.: 11/482,257

(22) Filed: Jul. 7, 2006

(65) Prior Publication Data

US 2006/0253196 A1 Nov. 9, 2006

Related U.S. Application Data

(62) Division of application No. 10/736,431, filed on Dec. 15, 2003, now abandoned.

(51) Int. Cl.
*A61F 2/16* (2006.01)
(52) U.S. Cl.
CPC .............. *A61F 2/1613* (2013.01); *A61F 2/1635* (2013.01); *A61F 2/1648* (2013.01); *A61F 2250/0003* (2013.01)
(58) Field of Classification Search
USPC ............. 623/6.19, 6.34, 6.37, 6.4, 6.41, 6.44, 623/6.49, 6.13
See application file for complete search history.

(56) References Cited

U.S. PATENT DOCUMENTS

| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,222,432 A | 12/1965 | Rene |
| 3,227,507 A | 1/1966 | Feinbloom |
| 3,305,294 A | 2/1967 | Alvarez |
| 3,339,997 A | 9/1967 | Wesley |
| 3,415,597 A | 12/1968 | Willard |

(Continued)

FOREIGN PATENT DOCUMENTS

| AU | 3225789 | 10/1989 |
| CH | 681687 A5 | 5/1993 |

(Continued)

OTHER PUBLICATIONS

U.S. Appl. No. 10/280,918, filed Aug. 5, 2003.

(Continued)

*Primary Examiner* — David H Willse
(74) *Attorney, Agent, or Firm* — Abbott Medical Optics Inc.

(57) ABSTRACT

An intraocular lens (30) having focusing capabilities permitting focusing movement of the lens (30) in response to normal ciliary body (24) movement incident to changes in the distance between the eye and an object under observation is provided. The lens (30) is designed for surgical implantation within the capsule (20) of an eye (10) and includes an optic (32) and an optic positioning element (33) which cooperate to form the lens (30). Accommodation is achieved by relying upon the thickening and thinning of the optic (32) as a result of the normal retracting and contracting of the ciliary body (24) in response to the distance of an object from the viewer.

16 Claims, 3 Drawing Sheets

(56) References Cited

U.S. PATENT DOCUMENTS

| | | |
|---|---|---|
| 3,420,006 A | 1/1969 | Barnett |
| 3,431,327 A | 3/1969 | Tsuetaki |
| 3,482,906 A | 12/1969 | Volk |
| 3,507,565 A | 4/1970 | Luis |
| 3,542,461 A | 11/1970 | Girard et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deltrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandle |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | DeCarle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,834,749 A | 5/1989 | Orlosky |

(56) References Cited

U.S. PATENT DOCUMENTS

| | | |
|---|---|---|
| 4,840,627 A | 6/1989 | Blumenthal |
| 4,842,601 A | 6/1989 | Smith |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Milege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wilkey et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Carabet |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |

(56) References Cited

U.S. PATENT DOCUMENTS

| | | | |
|---|---|---|---|
| 5,776,191 A | 7/1998 | Mazzocco | |
| 5,776,192 A | 7/1998 | McDonald | |
| 5,800,533 A | 9/1998 | Eggleston et al. | |
| 5,814,103 A | 9/1998 | Lipshitz et al. | |
| 5,824,074 A | 10/1998 | Koch | |
| 5,843,188 A | 12/1998 | McDonald | |
| 5,847,802 A | 12/1998 | Meneles et al. | |
| 5,864,378 A | 1/1999 | Portney | |
| 5,869,549 A | 2/1999 | Christ et al. | |
| RE36,150 E | 3/1999 | Gupta | |
| 5,876,441 A | 3/1999 | Shibuya | |
| 5,876,442 A | 3/1999 | Lipshitz et al. | |
| 5,885,279 A | 3/1999 | Bretton | |
| 5,895,422 A | 4/1999 | Hauber | |
| 5,898,473 A | 4/1999 | Seidner et al. | |
| 5,928,283 A | 7/1999 | Gross et al. | |
| 5,929,969 A | 7/1999 | Roffman | |
| 5,968,094 A | 10/1999 | Werblin et al. | |
| 5,984,962 A | 11/1999 | Anello et al. | |
| 6,013,101 A | 1/2000 | Israel | |
| 6,015,435 A | 1/2000 | Valunin et al. | |
| 6,050,970 A | 4/2000 | Baerveldt | |
| 6,051,024 A | 4/2000 | Cumming | |
| 6,063,118 A | 5/2000 | Nagamoto | |
| 6,083,261 A | 7/2000 | Callahan et al. | |
| 6,090,141 A | 7/2000 | Lindstrom | |
| 6,096,078 A | 8/2000 | McDonald | |
| 6,102,946 A | 8/2000 | Nigam | |
| 6,106,553 A | 8/2000 | Feingold | |
| 6,106,554 A | 8/2000 | Bretton | |
| 6,110,202 A | 8/2000 | Barraquer et al. | |
| 6,113,633 A * | 9/2000 | Portney | 623/6.32 |
| 6,117,171 A | 9/2000 | Skottun | |
| 6,120,538 A | 9/2000 | Rizzo, III et al. | |
| 6,136,026 A | 10/2000 | Israel | |
| 6,152,958 A | 11/2000 | Nordan | |
| 6,162,249 A | 12/2000 | Deacon et al. | |
| 6,176,878 B1 | 1/2001 | Gwon et al. | |
| 6,186,148 B1 | 2/2001 | Okada | |
| 6,197,058 B1 | 3/2001 | Portney | |
| 6,197,059 B1 | 3/2001 | Cumming | |
| 6,200,342 B1 | 3/2001 | Tassignon | |
| 6,210,005 B1 | 4/2001 | Portney | |
| 6,217,612 B1 | 4/2001 | Woods | |
| 6,221,105 B1 | 4/2001 | Portney | |
| 6,224,628 B1 | 5/2001 | Callahan et al. | |
| 6,228,115 B1 | 5/2001 | Hoffmann et al. | |
| 6,231,603 B1 | 5/2001 | Lang et al. | |
| 6,238,433 B1 | 5/2001 | Portney | |
| 6,241,777 B1 | 6/2001 | Kellan | |
| 6,251,312 B1 | 6/2001 | Phan et al. | |
| 6,258,123 B1 | 7/2001 | Young et al. | |
| 6,261,321 B1 | 7/2001 | Kellan | |
| 6,277,146 B1 | 8/2001 | Peyman et al. | |
| 6,277,147 B1 | 8/2001 | Christ et al. | |
| 6,280,471 B1 | 8/2001 | Peyman et al. | |
| 6,299,641 B1 | 10/2001 | Woods | |
| 6,302,911 B1 | 10/2001 | Hanna | |
| 6,322,213 B1 | 11/2001 | Altieri et al. | |
| 6,322,589 B1 | 11/2001 | Cumming | |
| 6,327,772 B1 | 12/2001 | Zadno-Azizi et al. | |
| 6,342,073 B1 | 1/2002 | Cumming et al. | |
| 6,358,280 B1 | 3/2002 | Herrick | |
| 6,364,906 B1 | 4/2002 | Baikoff et al. | |
| 6,387,126 B1 | 5/2002 | Cumming | |
| 6,399,734 B1 | 6/2002 | Hodd et al. | |
| 6,406,494 B1 | 6/2002 | Laguette et al. | |
| 6,423,094 B1 | 7/2002 | Sarfarazi | |
| 6,425,917 B1 | 7/2002 | Blake | |
| 6,443,985 B1 | 9/2002 | Woods | |
| 6,450,642 B1 | 9/2002 | Jethmalani et al. | |
| 6,454,802 B1 | 9/2002 | Bretton et al. | |
| 6,457,826 B1 | 10/2002 | Lett | |
| 6,464,725 B2 | 10/2002 | Skotton et al. | |
| 6,468,306 B1 | 10/2002 | Paul et al. | |
| 6,474,814 B1 | 11/2002 | Griffin | |
| 6,475,240 B1 | 11/2002 | Paul | |
| 6,478,821 B1 | 11/2002 | Laguette et al. | |
| 6,485,516 B2 | 11/2002 | Boehm | |
| 6,488,708 B2 | 12/2002 | Sarfarazi | |
| 6,494,911 B2 | 12/2002 | Cumming | |
| 6,503,276 B2 | 1/2003 | Lang et al. | |
| 6,517,577 B1 | 2/2003 | Callahan et al. | |
| 6,524,340 B2 | 2/2003 | Israel | |
| 6,533,813 B1 | 3/2003 | Lin et al. | |
| 6,533,814 B1 | 3/2003 | Jansen | |
| 6,536,899 B1 | 3/2003 | Fiala | |
| 6,547,822 B1 | 4/2003 | Lang | |
| 6,551,354 B1 | 4/2003 | Ghazizadeh et al. | |
| 6,554,859 B1 | 4/2003 | Lang et al. | |
| 6,558,420 B2 | 5/2003 | Green | |
| 6,589,550 B1 | 7/2003 | Hodd et al. | |
| 6,592,621 B1 | 7/2003 | Domino | |
| 6,598,606 B2 | 7/2003 | Terwee et al. | |
| 6,599,317 B1 | 7/2003 | Weinschenk, III et al. | |
| 6,616,691 B1 | 9/2003 | Tran | |
| 6,616,692 B1 | 9/2003 | Glick et al. | |
| 6,638,305 B2 | 10/2003 | Lagutte | |
| 6,638,306 B2 | 10/2003 | Cumming | |
| 6,645,246 B1 | 11/2003 | Weinschenk, III et al. | |
| 6,660,035 B1 | 12/2003 | Lang et al. | |
| 6,685,315 B1 | 2/2004 | De Carle | |
| 6,695,881 B2 | 2/2004 | Peng et al. | |
| 6,721,104 B2 | 4/2004 | Schachar et al. | |
| 6,730,123 B1 | 5/2004 | Klopotek | |
| 6,749,633 B1 | 6/2004 | Lorenzo et al. | |
| 6,749,634 B2 | 6/2004 | Hanna | |
| 6,761,737 B2 | 7/2004 | Zadno-Azizi et al. | |
| 6,764,511 B2 | 7/2004 | Zadno-Azizi et al. | |
| 6,767,363 B1 | 7/2004 | Bandhauer et al. | |
| 6,786,934 B2 | 9/2004 | Zadno-Azizi et al. | |
| 6,818,017 B1 | 11/2004 | Shu | |
| 6,818,158 B2 | 11/2004 | Pham et al. | |
| 6,827,738 B2 | 12/2004 | Willis et al. | |
| 6,846,326 B2 | 1/2005 | Zadno-Azizi et al. | |
| 6,855,164 B2 | 2/2005 | Glazier | |
| 6,858,040 B2 | 2/2005 | Nguyen et al. | |
| 6,884,261 B2 | 4/2005 | Zadno-Azizi et al. | |
| 6,884,262 B2 | 4/2005 | Brady et al. | |
| 6,884,263 B2 | 4/2005 | Valyunin et al. | |
| 6,899,732 B2 | 5/2005 | Zadno-Azizi et al. | |
| 6,926,736 B2 | 8/2005 | Peng et al. | |
| 6,930,838 B2 | 8/2005 | Schachar | |
| 6,942,695 B1 | 9/2005 | Chapoy et al. | |
| 7,018,409 B2 | 3/2006 | Glick et al. | |
| 7,021,760 B2 | 4/2006 | Newman | |
| 7,025,783 B2 | 4/2006 | Brady et al. | |
| 7,041,134 B2 | 5/2006 | Nguyen et al. | |
| 7,073,906 B1 | 7/2006 | Portney | |
| 7,087,080 B2 | 8/2006 | Zadno-Azizi et al. | |
| 7,097,660 B2 | 8/2006 | Portney | |
| 7,118,596 B2 | 10/2006 | Zadno-Azizi et al. | |
| 7,118,597 B2 | 10/2006 | Miller et al. | |
| 7,122,053 B2 | 10/2006 | Esch | |
| 7,125,422 B2 | 10/2006 | Woods | |
| 7,150,759 B2 | 12/2006 | Paul et al. | |
| 7,179,292 B2 | 2/2007 | Worst et al. | |
| 7,182,780 B2 | 2/2007 | Terwee et al. | |
| 7,186,266 B2 | 3/2007 | Peyman | |
| 7,188,949 B2 | 3/2007 | Bandhauer et al. | |
| 7,198,640 B2 | 4/2007 | Nguyen | |
| 7,217,288 B2 | 5/2007 | Esch et al. | |
| 7,220,279 B2 | 5/2007 | Nun | |
| 7,223,288 B2 | 5/2007 | Zhang et al. | |
| 7,226,478 B2 | 6/2007 | Ting et al. | |
| 7,238,201 B2 | 7/2007 | Portney et al. | |
| 7,247,168 B2 | 7/2007 | Esch et al. | |
| 7,261,737 B2 | 8/2007 | Esch et al. | |
| 7,344,617 B2 | 3/2008 | Dubrow | |
| 7,452,362 B2 | 11/2008 | Zadno-Azizi et al. | |
| 7,452,378 B2 | 11/2008 | Zadno-Azizi et al. | |
| 7,503,938 B2 | 3/2009 | Phillips | |
| 7,615,056 B2 | 11/2009 | Ayton et al. | |
| 7,645,300 B2 | 1/2010 | Tsai | |

(56) References Cited

U.S. PATENT DOCUMENTS

| | | |
|---|---|---|
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 2001/0001836 A1 | 5/2001 | Cumming |
| 2001/0004708 A1 | 6/2001 | Nagai |
| 2001/0012964 A1 | 8/2001 | Lang et al. |
| 2001/0016771 A1 | 8/2001 | Cumming |
| 2001/0018612 A1 | 8/2001 | Carson et al. |
| 2001/0039451 A1 | 11/2001 | Barnett |
| 2001/0044657 A1 | 11/2001 | Kellan |
| 2002/0002404 A1 | 1/2002 | Sarfarazi |
| 2002/0004682 A1 | 1/2002 | Zhou et al. |
| 2002/0011167 A1 | 1/2002 | Figov et al. |
| 2002/0045937 A1 | 4/2002 | Sarfarazi |
| 2002/0068971 A1 | 6/2002 | Cumming |
| 2002/0072795 A1 | 6/2002 | Green |
| 2002/0072796 A1 | 6/2002 | Hoffmann et al. |
| 2002/0095212 A1 | 7/2002 | Boehm |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0120329 A1 | 8/2002 | Lang et al. |
| 2002/0138140 A1 | 9/2002 | Hanna |
| 2002/0143395 A1 | 10/2002 | Skottun |
| 2002/0151973 A1 | 10/2002 | Arita et al. |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0018384 A1 | 1/2003 | Valyunin et al. |
| 2003/0020425 A1 | 1/2003 | Ricotti |
| 2003/0033013 A1 | 2/2003 | Callahan et al. |
| 2003/0050695 A1 | 3/2003 | Lin et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0074060 A1 | 4/2003 | Zadno-Azizi et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0093149 A1 | 5/2003 | Glazier |
| 2003/0105522 A1 | 6/2003 | Glazier |
| 2003/0109925 A1 | 6/2003 | Ghazizadeh et al. |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015235 A1 | 1/2004 | Worst et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0106992 A1 | 6/2004 | Lang et al. |
| 2004/0111151 A1 | 6/2004 | Paul et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0162612 A1 | 8/2004 | Portney et al. |
| 2004/0167621 A1 | 8/2004 | Peyman |
| 2004/0181279 A1 | 9/2004 | Nun |
| 2004/0215340 A1 | 10/2004 | Hanna et al. |
| 2004/0230299 A1 | 11/2004 | Simpson et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0049700 A1 | 3/2005 | Zadno-Azizi et al. |
| 2005/0055092 A1 | 3/2005 | Nguyen et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0113914 A1 | 5/2005 | Miller et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0228401 A1 | 10/2005 | Zadno-Azizi et al. |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0095127 A1 | 5/2006 | Feingold et al. |
| 2006/0098162 A1 | 5/2006 | Bandhauer et al. |
| 2006/0100702 A1 | 5/2006 | Peyman |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0209431 A1 | 9/2006 | Spivey |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno-Azizi et al. |
| 2007/0032866 A1 | 2/2007 | Portney |
| 2007/0050025 A1 | 3/2007 | Nguyen et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106379 A1 | 5/2007 | Messner |
| 2007/0106381 A1 | 5/2007 | Blake |
| 2007/0108643 A1 | 5/2007 | Zadno-Azizi et al. |
| 2007/0129798 A1 | 6/2007 | Chawdhary |
| 2007/0135915 A1 | 6/2007 | Klima |
| 2007/0156236 A1 | 7/2007 | Stenger |
| 2007/0213817 A1 | 9/2007 | Esch et al. |
| 2007/0244561 A1 | 10/2007 | Ben Nun |
| 2007/0258143 A1 | 11/2007 | Portney |
| 2007/0260309 A1 | 11/2007 | Richardson |
| 2007/0282247 A1 | 12/2007 | Desai et al. |
| 2007/0299487 A1 | 12/2007 | Shadduck |
| 2008/0004699 A1 | 1/2008 | Ben Nun |
| 2008/0125790 A1 | 5/2008 | Tsai et al. |
| 2008/0140192 A1 | 6/2008 | Humayun et al. |

(56) References Cited

U.S. PATENT DOCUMENTS

| | | |
|---|---|---|
| 2008/0161913 A1 | 7/2008 | Brady |
| 2008/0161914 A1 | 7/2008 | Brady |
| 2008/0300680 A1 | 12/2008 | Joshua |
| 2009/0012609 A1 | 1/2009 | Geraghty |
| 2009/0234448 A1 | 9/2009 | Weeber et al. |
| 2009/0248152 A1 | 10/2009 | Bumbalough |
| 2010/0057203 A1 | 3/2010 | Glick et al. |
| 2010/0228346 A1 | 9/2010 | Esch |
| 2011/0035001 A1 | 2/2011 | Woods |
| 2012/0046744 A1 | 2/2012 | Woods et al. |

FOREIGN PATENT DOCUMENTS

| | | |
|---|---|---|
| DE | 2702117 | 7/1978 |
| DE | 3246306 | 6/1984 |
| DE | 4038088 | 6/1992 |
| DE | 19501444 | 7/1996 |
| DE | 19951148 A1 | 4/2001 |
| DE | 10059482 A1 | 6/2002 |
| DE | 10125829 A1 | 11/2002 |
| EP | 0064812 | 11/1982 |
| EP | 162573 A2 | 11/1985 |
| EP | 212616 A2 | 3/1987 |
| EP | 0246216 | 11/1987 |
| EP | 0 328 117 A2 | 8/1989 |
| EP | 0329981 | 8/1989 |
| EP | 331457 A2 | 9/1989 |
| EP | 0 337 390 A2 | 10/1989 |
| EP | 336877 A1 | 10/1989 |
| EP | 342895 A2 | 11/1989 |
| EP | 0351471 | 1/1990 |
| EP | 0356050 | 2/1990 |
| EP | 488835 A1 | 6/1992 |
| EP | 0507292 | 10/1992 |
| EP | 0566170 | 10/1993 |
| EP | 0601845 | 6/1994 |
| EP | 605841 A1 | 7/1994 |
| EP | 0691109 | 1/1996 |
| EP | 0897702 | 2/1999 |
| EP | 766540 B1 | 8/1999 |
| EP | 766540 B1 | 8/1999 |
| EP | 1108402 A2 | 6/2001 |
| FR | 2666504 A1 | 3/1992 |
| FR | 2666735 A1 | 3/1992 |
| FR | 2681524 A1 | 3/1993 |
| FR | 2778093 A1 | 11/1999 |
| FR | 2784575 A1 | 4/2000 |
| GB | 939016 A | 10/1963 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| JP | 0211134 | 1/1990 |
| JP | 2126847 | 5/1990 |
| JP | H06508279 | 9/1994 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 90/00889 | 2/1990 |
| WO | 93/05733 | 4/1993 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/27825 | 8/1997 |
| WO | 97/43984 | 11/1997 |
| WO | WO9805273 A1 | 2/1998 |
| WO | 98/56315 | 12/1998 |
| WO | 9920206 A1 | 4/1999 |
| WO | 9929266 A1 | 6/1999 |
| WO | 00/61036 | 4/2000 |
| WO | 0021467 A1 | 4/2000 |
| WO | 00/27315 | 5/2000 |
| WO | 0059407 A1 | 10/2000 |
| WO | 00/66039 | 11/2000 |
| WO | 0066041 A1 | 11/2000 |
| WO | 0108605 A1 | 2/2001 |
| WO | 01/19288 | 3/2001 |
| WO | WO0119289 A1 | 3/2001 |
| WO | 0128144 A1 | 4/2001 |
| WO | 01/34066 | 5/2001 |
| WO | 01/34067 | 5/2001 |
| WO | 0156510 A1 | 8/2001 |
| WO | 0160286 A1 | 8/2001 |
| WO | 0164136 A2 | 9/2001 |
| WO | 0166042 A1 | 9/2001 |
| WO | WO0164135 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |
| WO | 02/19949 | 3/2002 |
| WO | 02058391 A2 | 7/2002 |
| WO | 02071983 A1 | 9/2002 |
| WO | 02098328 A1 | 12/2002 |
| WO | 03009051 A2 | 1/2003 |
| WO | 03/015669 | 2/2003 |
| WO | 03015657 A2 | 2/2003 |
| WO | 03/034949 | 5/2003 |
| WO | 03049646 A2 | 6/2003 |
| WO | 03/059208 | 7/2003 |
| WO | 03057081 A2 | 7/2003 |
| WO | 03059196 A2 | 7/2003 |
| WO | 03/075810 | 9/2003 |
| WO | 03084441 A1 | 10/2003 |
| WO | 03092552 A1 | 11/2003 |
| WO | 04000171 A1 | 12/2003 |
| WO | 2004020549 A1 | 3/2004 |
| WO | 2004037127 A2 | 5/2004 |
| WO | 2005/018504 | 3/2005 |
| WO | 2005019871 A2 | 3/2005 |
| WO | WO03082147 A3 | 8/2005 |
| WO | WO2005115278 A1 | 12/2005 |
| WO | 2007/040964 | 4/2007 |
| WO | 2007-067872 | 6/2007 |
| WO | 2007/067872 | 6/2007 |
| WO | 2008077795 A2 | 7/2008 |
| WO | 2008079671 A1 | 7/2008 |
| WO | 2009021327 A1 | 2/2009 |
| WO | 2010093823 A2 | 8/2010 |
| ZA | 888414 | 11/1988 |

OTHER PUBLICATIONS

U.S. Appl. No. 10/280,937, filed Oct. 25, 2005.
Menezo et al. Endothelial study of iris-claw phakic lens: four year follow-up. *J. Cataract Refract. Surg.*, Aug. 24, 1998. pp. 1039-1049.
AMO Specs, Model AC-21B, 1992, 5 pages.
Study Design of Nuvita, Mar. 20, 1997, 5 pages.
Program from ASCRS Symposium showing video tape between Apr. 10-14, 1999, 2 pages.
DVD titled "New elliptical accommodative IOL for cataract surgery" shown at ASCRS Symposium on Apr. 10, 1999.

(56) References Cited

OTHER PUBLICATIONS

International Search Report for Application No. PCT/US2004/41839, mailed on May 11, 2005, 1 page.
Supplementary European Search Report of EP Patent Application No. EP04814069, dated Jul. 12, 2007, 1 page total.
U.S. Appl. No. 09/656,661, filed Sep. 7, 2000.
U.S. Appl. No. 09/721,072, filed Nov. 22, 2000.
Altan-Yaycioglu R., et al., "Pseudo-accommodation with Intraocular Lenses Implanted in the Bag," Journal of Refractive Surgery, 2002, vol. 18 (3), pp. 271-275.
Chiron, Clemente Optfit Model SP525, Brochure Translation, Jul. 12, 1998.
Cohen A.L., "Practical Design of a Bifocal Hologram Contact Lens of Intraocular Lens," Applied Optics, 1992, vol. 31 (19), pp. 3750-3754.
Klien S.A., "Understanding the Diffractive Bifocal Contact Lens," Optometry and Vision Science, 1993, vol. 70 (6), pp. 439-460.
Co-pending U.S. Appl. No. 09/390,380, filed Sep. 3, 1999.
Co-pending U.S. Appl. No. 09/522,326, filed Mar. 9, 2000.
Co-pending U.S. Appl. No. 09/532,910, filed Mar. 22, 2000.
Co-pending U.S. Appl. No. 09/565,036, filed May 3, 2000.
Co-pending U.S. Appl. No. 09/631,223, filed Aug. 2, 2000.
Co-pending U.S. Appl. No. 09/657,251, filed Sep. 7, 2000.
Co-pending U.S. Appl. No. 09/657,325, filed Sep. 7, 2000.
Co-pending U.S. Appl. No. 09/795,929, filed Feb. 28, 2001.
Co-pending U.S. Appl. No. 09/822,040, filed Mar. 30, 2001.
Co-pending U.S. Appl. No. 10/020,853, filed Dec. 11, 2001.
Co-pending U.S. Appl. No. 10/635,423, filed Aug. 6, 2003.
Co-pending U.S. Appl. No. 11/618,325, filed Dec. 29, 2006.
Co-pending U.S. Appl. No. 11/618,411, filed Dec. 29, 2006.
Co-pending U.S. Appl. No. 11/966,365, filed Dec. 28, 2007.
Mandell R.B., "Contact Lens Practice", 4th Edition, Charles C. Thomas Publishers, 1988, 11 pages.
"Accommodation in Pseudophakia," in: Percival SPB Color atlas of lens implantation, Chap. 25, St Louis, ed., Mosby, United States, 1991, pp. 159-162.

\* cited by examiner

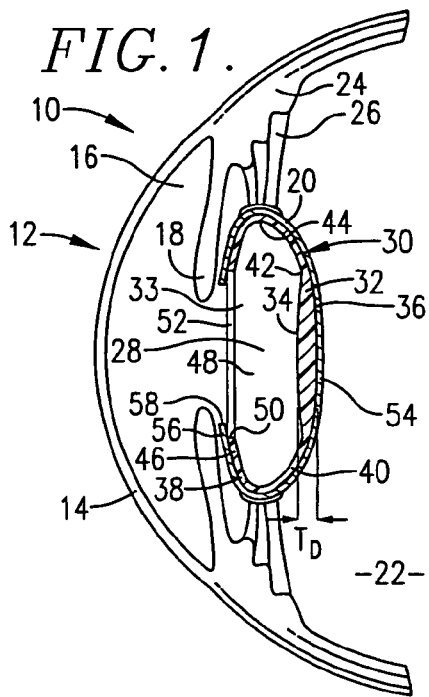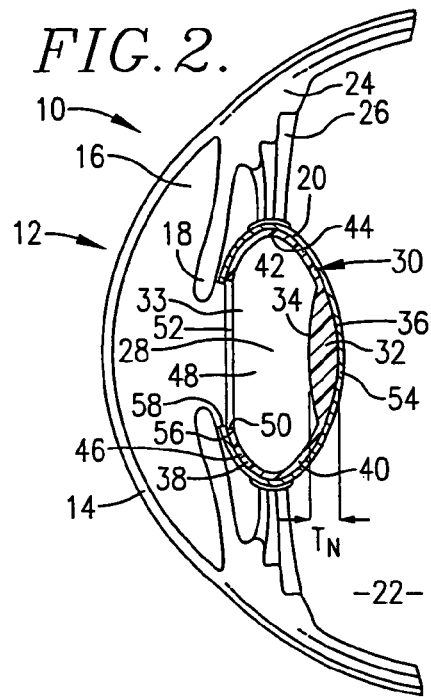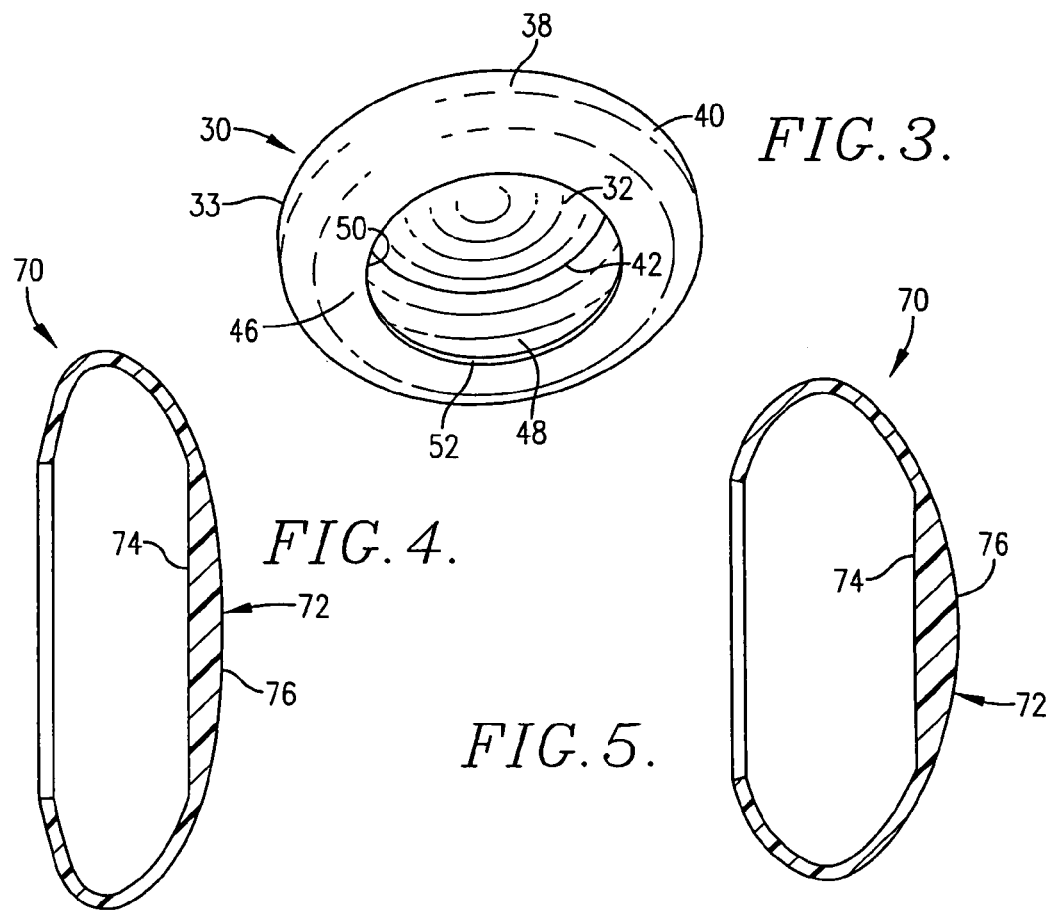

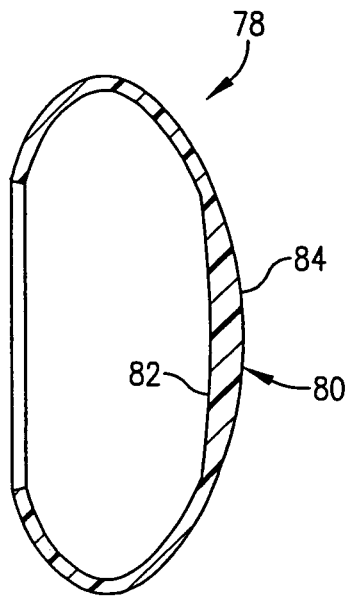
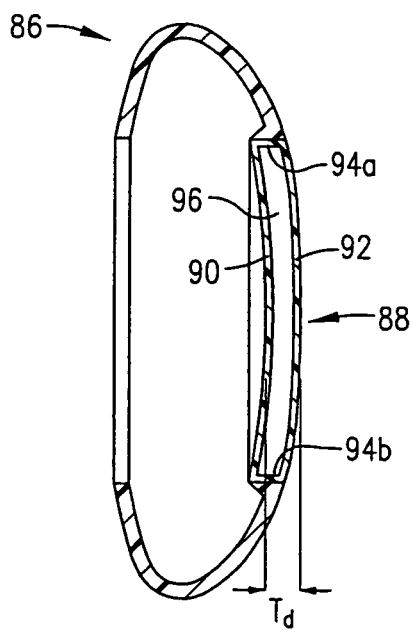
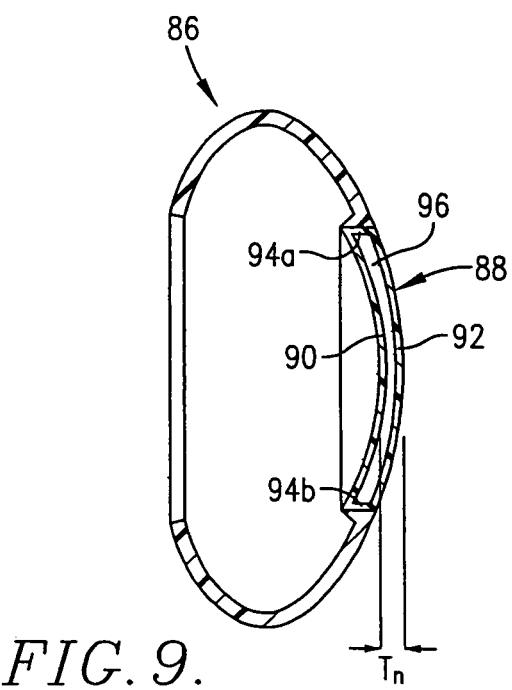

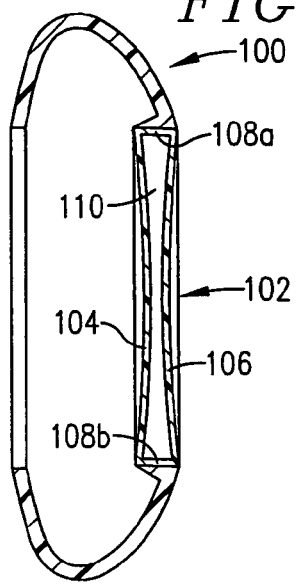
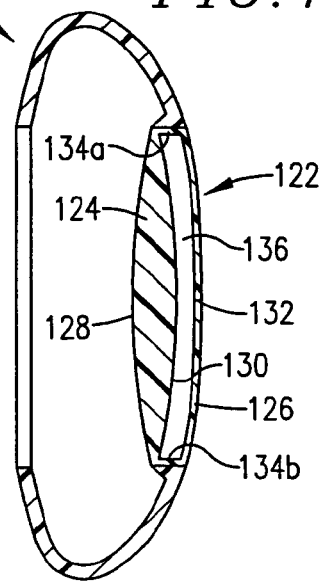
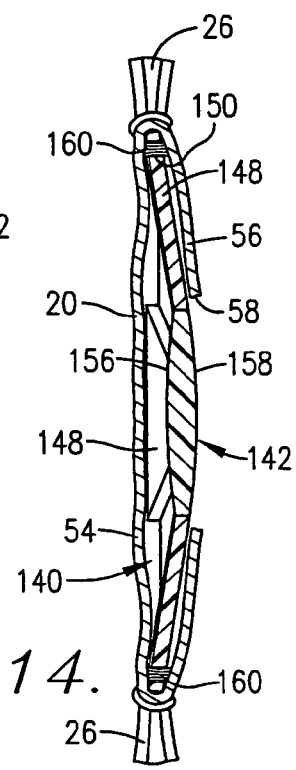
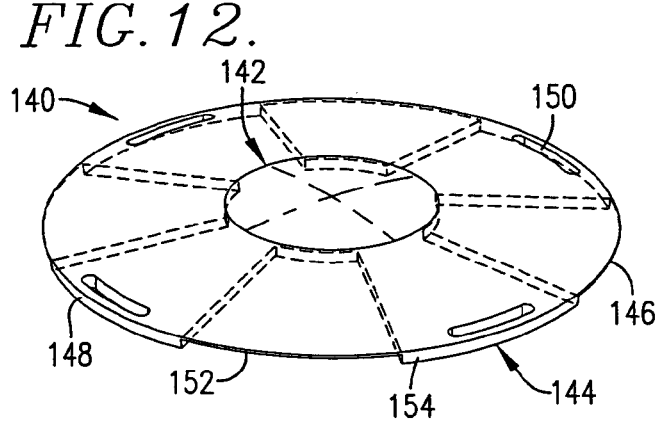
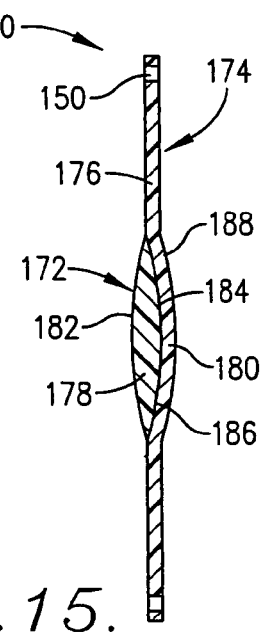
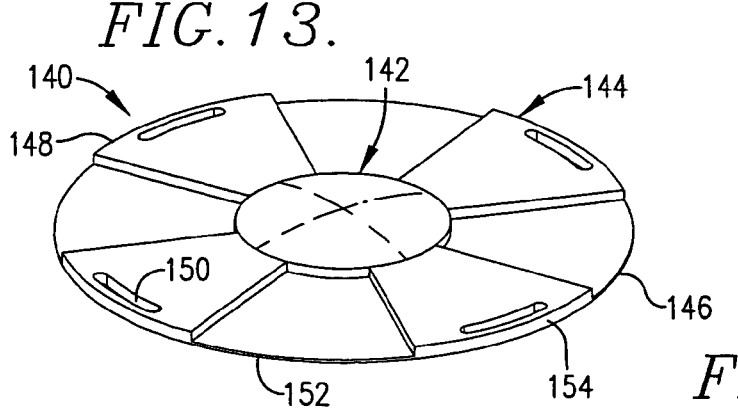

INTRAOCULAR LENS IMPLANT HAVING POSTERIOR BENDABLE OPTIC

RELATED APPLICATION

This application is a divisional application which claims priority to U.S. application No. Ser. 10/736,431, filed Dec. 15, 2003, now abandoned, and which is incorporated herein in its entirety.

BACKGROUND OF THE INVENTION

1. Field of the Invention

The present invention relates to accommodating intraocular lenses which can be surgically implanted as a replacement for the natural crystalline lens in the eyes of cataract patients.

2. Description of the Prior Art

Cataracts occur when the crystalline lens of the eye becomes opaque. The cataracts may be in both eyes and, being a progressive condition, may cause fading vision and eventual blindness. Cataracts were once surgically removed along with the anterior wall of the capsule of the eye. The patient then wore eyeglasses or contact lenses which restored vision but did not permit accommodation and gave only limited depth perception.

The first implant of a replacement lens within the eye occurred in 1949 and attempted to locate the replacement lens in the posterior chamber of the eye behind the iris. Problems such as dislocation after implantation forced abandonment of this approach, and for some period thereafter intraocular lenses were implanted in the anterior chamber of the eye.

Others returned to the practice of inserting the lens in the area of the eye posterior to the iris, known as the posterior chamber. This is the area where the patient's natural crystalline lens is located. When the intraocular lens is located in this natural location, substantially normal vision may be restored to the patient and the problems of forward displacement of vitreous humor and retina detachment encountered in anterior chamber intraocular lenses are less likely to occur. Lenses implanted in the posterior chamber are disclosed in U.S. Pat. Nos. 3,718,870, 3,866,249, 3,913,148, 3,925,825, 4,014,049, 4,041,552, 4,053,953, and 4,285,072. None of these lenses has focusing capability.

Lenses capable of focusing offer the wearer the closest possible substitute to the crystalline lens. U.S. Pat. No. 4,254,509 to Tennant discloses a lens which moves in an anterior direction upon contraction of the ciliary body, and which is located anterior to the iris. Though providing focusing capabilities, it presents the same disadvantages as other anterior chamber lenses.

U.S. Pat. No. 4,409,691 to Levy is asserted to provide a focusable intraocular lens positioned within the capsule. This lens is located in the posterior area of the capsule and is biased toward the fovea or rear of the eye. The '691 lens is deficient because it requires the ciliary muscle to exert force through the zonules on the capsule in order to compress the haptics inward and drive the optic forward for near vision. However, the ciliary muscles do not exert any force during contraction because the zonules, being flexible filaments, exert only tension, not compression on the capsule. The natural elasticity of the lens causes the capsule to become more spherical upon contraction of the ciliary muscle. Thus, there is no inward force exerted on the capsule to compress the haptics of the Levy lens, and therefore accommodate for near vision.

U.S. Pat. No. 5,674,282 to Cumming is directed towards an accommodating intraocular lens for implanting within the capsule of an eye. The Cumming lens comprises a central optic and two plate haptics which extend radially outward from diametrically opposite sides of the optic and are movable anteriorly and posteriorly relative to the optic. However, the Cumming lens suffers from the same shortcomings as the Levy lens in that the haptics are biased anteriorly by pressure from the ciliary bodies. This will eventually lead to pressure necrosis of the ciliary body.

There is a need for an intraocular lens implant capable of focusing in a manner similar to the natural lens. This lens implant should be readily insertable into the capsule and should last for a substantial number of years without damaging any of the eye components.

SUMMARY OF THE INVENTION

The present invention fills this need by providing an intraocular lens with focusing capabilities which is safe for long-term use in an eye.

In more detail, the lens of the invention comprises an optic coupled to an optic positioning element. The optic positioning element is preferably balloon-shaped or preferably comprises an outwardly extending disc (optionally with thicker, radially extending "winged" portions separated by thin membranes). The optic is resilient and can be formed of a solid material (e.g., silicone) or can be gas-filled.

As a result of the size and shape of the inventive lens and the material of which the optic is formed, the focusing action of the natural lens is simulated. That is, the ciliary body of the eye continues to exert a muscular force radially outward from the center of the capsule through the zonular fibers so as to alter the thickness of the optic, resulting in a decrease in light convergence as is necessary for viewing objects distant from the viewer. When viewing an object close to the viewer, the ciliary body contracts, thus releasing the outward pull on the zonular fibers. This alters the thickness of the optic to result in an increase in light convergence as is necessary for viewing nearby objects.

The optic can be one of many shapes as described in more detail below. Furthermore, the optic can be formed of a solid, liquid, or gel refractive material, or the optic can be gas-filled (e.g., air) so long as the chosen materials are safe for use in the eye. The shape of the optic and the material of which the optic is formed are dependent upon one another. That is, the shape is chosen based upon the refractive index of the material used to form the optic, and this choice is made to result in an optic which will highly converge light upon contraction of the ciliary body. Thus, if the refractive index of the optic material is greater than about 1.33 (the refractive index of the fluids within the eye), then optic shapes such as meniscus, planoconvex, and biconvex would converge light. On the other hand, if the refractive index of the optic material is less than about 1.33, then optic shapes such as biconcave and planoconcave would converge light.

BRIEF DESCRIPTION OF THE DRAWING FIGURES

FIG. 1 is a vertical sectional view showing placement of the lens of the invention within the capsule of an eye, with the eye focused on an object distant from the viewer;

FIG. 2 is a vertical sectional view showing the change in shape of the lens of FIG. 1 when focused on an object near the viewer;

FIG. 3 is a perspective view of the lens of FIGS. 1-2, shown in its resting state;

FIG. 4 is a vertical sectional view showing another embodiment of the inventive lens, with the lens being focused on an object distant from the viewer;

FIG. 5 is a vertical sectional view showing the change in shape of the lens of FIG. 4 when focused on an object near the viewer;

FIG. 6 is a vertical sectional view showing another embodiment of the inventive lens, with the lens being focused on an object distant from the viewer;

FIG. 7 is a vertical sectional view showing the change in shape of the lens of FIG. 6 when focused on an object near the viewer;

FIG. 8 is a vertical sectional view showing another embodiment of the inventive lens having a gas-filled optic, with the lens being focused on an object distant from the viewer;

FIG. 9 is a vertical sectional view showing the change in shape of the lens of FIG. 8 when focused on an object near the viewer;

FIG. 10 is a vertical sectional view showing another embodiment of the inventive lens where the lens has a gas-filled optic;

FIG. 11 is a vertical sectional view showing another inventive lens having a combination optic;

FIG. 12 is an upper perspective view of another lens according to the invention utilizing a resilient optic with a different type of optic positioning element;

FIG. 13 is a lower perspective view of the lens of FIG. 12;

FIG. 14 is a sectional view of the lens shown in FIGS. 12-13; and

FIG. 15 is a sectional view of another embodiment of the lens of FIG. 12, where the optic is a combination optic.

DETAILED DESCRIPTION OF THE PREFERRED EMBODIMENTS

Referring now to the drawings, the present invention is in the form of an intraocular lens for surgical replacement of the human lens in the treatment of cataracts in the human eye. FIG. 1 shows the various components of the human eye pertinent to this invention. Briefly, the eye 10 includes a frontal portion 12 and a rearward portion (not shown). The frontal portion 12 of the eye 10 is covered by a cornea 14 which encloses and forms an anterior chamber 16. The anterior chamber 16 contains aqueous fluid and is bounded at the rear by an iris 18. The iris 18 opens and closes to admit appropriate quantities of light into the inner portions of the eye 10. The eye 10 includes a capsule 20 which ordinarily contains the natural crystalline lens. When the eye 10 focuses, the capsule 20 changes shape to appropriately distribute the light admitted through the cornea 14 and the iris 18 to the retina (not shown) at the rearward portion of the eye 10.

Although not shown in the accompanying figures, the retina is composed of rods and cones which act as light receptors. The retina includes a fovea which is a rodless portion which provides for acute vision. The outside of the rearward or posterior portion of the eye 10 is known as the sclera. The sclera joins with, and forms a portion of, the covering for the optic nerve. Images received by the retina are transmitted through the optic nerve to the brain. The area between the retina and the capsule 20 is occupied by vitreous fluid. Finally, the eye 10 includes a ciliary muscle or body 24 having zonular fibers 26 (also referred to as zonules) which are attached to the capsule 20.

Ocular adjustments for sharp focusing of objects viewed at different distances is accomplished by the action of the ciliary body 24 on the capsule 20 and crystalline lens (which would be located at numeral 28 in the natural, unmodified eye) through the zonular fibers 26. The ciliary body 24 contracts, allowing the capsule 20 to return to a more spherical shape for viewing objects that are nearer the viewer. When the ciliary body 24 retracts and pulls on the zonular fibers 26 to make the capsule 20 more discoid, objects at a distance can be viewed in proper focus.

1. Lens Embodiment of FIGS. 1-3

Referring to FIGS. 1-3, the inventive lens is an accommodating lens 30 which includes a biconvex optic 32 and an optic positioning element 33. The optic 32 comprises a convex anterior surface 34 and a convex posterior surface 36. The optic positioning element 33 comprises a resilient body 38. Resilient body 38 comprises an outer wall 40 which extends radially from optic 32. Resilient body 38 is preferably integral and essentially flush with optic 32 at optic perimeter 42 where wall 40 joins optic 32. Wall 40 then curves to form a bight 44 and converges on the posterior side 46 of lens 30. Wall 40 forms a chamber 48 and terminates at location 50 to form an opening 52 which communicates with the chamber 48, allowing fluids to enter and fill the chamber 48.

Preferably, the overall shape of lens 30 in its original resting, non-deformed shape generally conforms to the shape of capsule 20 when capsule 20 is focused to view an object near the viewer (FIGS. 1 and 3). Thus, outer wall 40 of the resilient body 38 cooperates with optic 32 to form a lens having an overall discoid or saucer-like shape as best shown in FIG. 1. The lens 30 is of sufficient size that optic 32 mildly urges against the posterior wall 54 of the capsule 20, while the posterior side 46 of lens 30 urges against the anterior wall 56 of the capsule 20. The optic 30 is formed of a resilient, bendable material which allows for changes in thickness of optic 30.

Intraocular lens 30 substitutes both locationally and functionally for the original, natural, crystalline lens (which would normally be at location 28). To insert the lens 30 into the capsule 20, an ophthalmic surgeon would remove the natural lens (and thus the cataracts) by conventional methods, leaving an opening 58 in the anterior wall 56 of the capsule 20. Lens 30 is then folded into a compact size for insertion into the capsule 20 through the opening 58. Once inserted, the capsule 20 is filled with fluids (e.g., saline solution) which enter the chamber 48 of the lens 30, causing the lens 30 to return to its original, non-deformed state as shown in FIGS. 1 and 3. There is no need to suture the lens 30 to the capsule 20 because, due to the size and shape of the lens 30 as described above, the lens 30 will not rotate or shift within the capsule 20.

Implantation of the inventive lens 30 restores normal vision because, not only does the lens 30 replace the patient's occluded natural lens, but the normal responses of the ciliary body 24 cooperate with the lens 30 during focusing. In FIG. 1, the capsule 20 is shaped for viewing an object distant from the eye 10. That is, in order to view an object distant from the viewer, the ciliary body 24 has retracted, thus pulling on the zonular fibers 26, making the capsule 20 (and thus the lens 30) more discoid in shape. This change in shape causes the optic 32 to become thinner (i.e., there is a decrease in the horizontal depth of the optic 32) so that it has a thickness $T_D$. As used herein, the thickness of the optic is intended to be the thickness at approximately the center of the optic.

Optic 32 is formed of a solid, liquid, or gel material (e.g., silicone) so it has a refractive index greater than that of the surrounding fluid in the eye (i.e., greater than 1.33). This refractive index, combined with the thinness of optic 32 as shown in FIG. 1, results in a less convergent lens which makes distance viewing possible.

Referring to FIG. 2, the ciliary body 24 has contracted, making the capsule 20 more spheroid in shape. As a result, the optic 32 has had an increase in thickness to a thickness of $T_N$. The thickness increase should be such that $T_N$ is at least about 1.1 times, preferably at least about 1.2 times, and more preferably from about 1.2-1.4 times that of $T_D$ when a force of from about 1-9 grams, and preferably from about 6-9 grams, is applied to the optic positioning element (more specifically, to the outer edges of the optic positioning element or around the equatorial region of the optic positioning element). As used herein, the force is a measure of an inwardly directed force in the plane of the equator equally distributed over 360 degrees around the equator.

This increase in optic thickness combined with the fact that the refractive index of the optic 32 is greater than 1.33 (and preferably at least about 1.36, more preferably at least about 1.4, and even more preferably at least about 1.5) results in an increased convergence of light, thus enabling the eye to see objects near the viewer. The lens 30 thus follows the eye's natural physiology for focusing to provide a substitute means of optical accommodation.

2. Embodiment of FIGS. 4-5

While the anterior surface 34 and the posterior surface 36 of the lens 30 of FIGS. 1-3 are both convex, the shapes of these surfaces can be varied depending upon the user's eyesight. One such variation is shown in FIGS. 4-5.

FIGS. 4-5 show a lens 70 which is similar in construction to the lens 30 of FIGS. 1-3 with the exception of the optic construction. That is, lens 70 includes a planoconvex optic 72. The optic 72 comprises a planar anterior surface 74 and a convex posterior surface 76. Lens 70 operates to provide accommodation in the same manner as discussed above with respect to lens 30.

3. Embodiment of FIGS. 6-7

FIGS. 6-7 show a lens 78 which is similar in construction to the lens 30 of FIGS. 1-3 with the exception of the optic construction. Lens 78 includes an optic 80 whose cross-section is meniscus in shape. That is, the optic 80 comprises a concave anterior surface 82 and a convex posterior surface 84 so that the curves of surfaces 82, 84 follow the same general direction of curvature. Lens 78 operates to provide accommodation in the same manner as discussed above with respect to lens 30.

4. Embodiment of FIGS. 8-9

FIGS. 8-9 show a lens 86 which is also similar in construction to the lens 30 of FIGS. 1-3 with the exception of the optic construction. Lens 86 includes an optic 88 whose cross-section is meniscus in shape. That is, the optic 88 comprises a concave anterior wall 90 and a convex posterior wall 92 so that the curves of walls 90, 92 follow the same general direction of curvature.

While lens 86 includes a meniscus-shaped optic 88 like that of the embodiment of FIGS. 6-7, the optic 88 is very different from optic 80 of lens 78 in that optic 88 is gas-filled. That is, walls 90, 92 cooperate with endwalls 94a,b to form a chamber 96. Chamber 96 is filled with a gas. While any biologically safe gas is acceptable, the preferred gas is simply air. Also, walls 90, 92 and endwalls 94a,g can be formed of the same materials described previously with respect to optic and optic positioning element materials.

Although lens 86 has a gas-filled optic 88 rather than a solid optic, lens 86 still operates to provide accommodation in a somewhat similar manner as discussed above with respect to lens 30. In more detail and referring to FIG. 8, the lens 86 is shaped for viewing an object distant from the viewer. That is, in order to view an object distant from the viewer, the ciliary body (not shown) has retracted, thus pulling on the zonular fibers and making the lens 86 more discoid in shape. This change in shape causes the optic 88 to become thicker (i.e., there is an increase in the horizontal depth of the optic 88 or there is an increase in the distance between wall 90 and wall 92) so that the optic 88 has a thickness $T_d$. However, because optic 88 is filled with a gas, a thicker optic 88 results in a lesser convergence of light because the gas has a refractive index which is lower than the refractive index of the fluids in the eye (i.e., less than about 1.3, preferably less than about 1.2, and more preferably less than about 1.0), thus making optic 88 suitable for distance viewing.

Referring to FIG. 9, the ciliary body (not shown) has contracted, making the lens 86 more spheroid in shape. As discussed with previous embodiments, a solid optic would incur an increase in thickness as a result of the contraction. However, due to the fact that optic 88 is gas-filled, the distance between wall 90 and wall 92 decreases, thus causing optic 88 to have a decrease in thickness to a thickness of $T_n$. This decrease in optic thickness results in an increased convergence of light, thus enabling the eye to see objects near the viewer. Thus, the thickness decrease when a force of from about 1-9 grams, and preferably from about 6-9 grams, is applied to the optic positioning element (more specifically, to the outer edges of the optic positioning element or around the equatorial region of the optic positioning element) should be such that $T_d$ is at least about 1.2 times, preferably at least about 1.3 times, and more preferably from about 1.3-1.35 times that of $T_n$.

5. Embodiment of FIG. 10

FIG. 10 shows a lens 100 which is similar in overall construction to the lens of FIGS. 8-9 except that lens 100 includes a biconcave optic 102. Optic 102 includes an anterior, concave wall 104, a posterior concave wall 106, and a pair of endwalls 108a,b. Walls 104 and 106 cooperate with endwalls 108a,b to form gas-filled chamber 110 which is filled with a biologically safe gas such as air. The lens 100 operates to provide accommodation in a manner similar to that described with respect to lens 86 of FIGS. 8-9.

6. Embodiment of FIG. 11

FIG. 11 shows a lens 120 which is constructed in a manner similar to that of the preceding lens embodiments with the exception of the optic construction. Lens 120 includes a combination optic 122 which combines aspects of the optics shown in FIGS. 1-7 with the type of optic disclosed in FIGS. 8-10. That is, the optic 122 comprises a biconvex, solid optic 124 and a gas-filled optic 126. Optic 124 includes a convex, anterior surface 128 and a convex posterior surface 130. Optic 126 includes a convex, posterior wall 132 and endwalls 134a,b which cooperate with convex posterior surface 130 of optic 124 to form a gas-filled chamber 136. Again, any biologically safe gas is acceptable, although air is preferred.

The lens 120 operates to provide accommodation in a manner similar to that described with respect to lens 86 of FIGS. 8-10. That is, the gas-filled optic 126 will become thinner, and the solid optic 124 may become thicker upon contraction of the ciliary body, thus causing an increased convergence of light to allow for near viewing. Upon retraction of the ciliary body, the opposite will occur. That is, the lens 120 will become more discoid in shape so that the gas-filled optic 126 will become thicker while the solid optic 124 will become thinner, thus causing a decreased convergence of light to allow for distance viewing.

7. Embodiment of FIGS. 12-14

FIGS. 12-15 illustrate embodiments where a different type of optic positioning element is utilized. Referring to FIGS. 12-13, the lens includes an optic 142 and an optic positioning element 144. Optic 142 can be of any known optic construction, or it can be any of the inventive optics disclosed herein.

Optic positioning element 144 comprises a skirt 146 which includes a plurality of radially extending elements 148. In the embodiment shown, elements 148 comprise respective openings 150. The respective sizes and shapes of openings 150 are not critical so long as they are capable of allowing fibrosis of the tissue. Furthermore, openings 150 can be omitted if desired.

Elements 148 are joined to one another by thin membranes 152. Alternately, optic positioning element 144 can simply include a circular or disc-shaped haptic having a substantially uniform thickness (i.e., rather than thicker radially extending elements 148 and thinner membranes 152) extending from the optic.

Elements 148 and membranes 152 are generally formed of the same material (e.g., silicones, acrylates) but with a difference in thicknesses, although the material can be different, and the selection of material is not critical so long as it is biologically safe and at least somewhat resilient. It will be appreciated that the respective thicknesses of elements 148 and membranes 152 can be adjusted as necessary by one of ordinary skill in the art. Ideally, the elements 148 will be of sufficient respective thicknesses to provide resistance to the force created on the outer edges 154 of the elements 148 by the contraction of the ciliary body. The respective thicknesses of the membranes 152 should be such that the flexibility of the overall skirt 146 is maintained while being resistant to tearing.

FIG. 14 shows one type of possible optic construction for use with this type of optic positioning element 144. In this embodiment, lens 160 is shown within a capsule 20 of an eye. The optic 142 includes a posterior convex surface 156 and an anterior convex surface 158. In the embodiment shown, optic 142 is integrally formed with elements 148, although this is not mandatory. Finally, FIG. 14 demonstrates the formation of fibrin 160 (fibrosis) through openings 150.

Lens 140 would operate to provide accommodation in a manner similar to that described with respect to lens 30 of FIGS. 1-3. That is, the ciliary body (not shown) would retract or contract as necessary, thus either pulling on the zonular fibers 26 or releasing the pull on the zonular fibers 26. Due to the fibrin 160 formed through openings 150, this would necessarily result in an outward force on elements 148 (resulting in the thinning of optic 142) or the release of that outward force (resulting in the thickening of optic 142). Because optic 142 is formed of a material having a refractive index of greater than 1.33, thickening of optic 142 would result in increased convergence of light for near viewing and thinning of optic 142 would result in decreased convergence of light for distance viewing.

8. Embodiment of FIG. 15

FIG. 15 shows another lens according to the invention. This lens is constructed similarly to that of FIGS. 12-14 except that a different optic is utilized. Specifically, lens 170 comprises a combination optic 172 and an optic positioning element 174. Optic positioning element 174 is similar to optic positioning element 144 of FIGS. 12-14 in that it includes a plurality of radially extending elements 176 connected via thin membranes (not shown). Combination optic 172 comprises a biconvex optic 178 and a meniscus optic 180. Biconvex optic 178 includes a convex, anterior surface 182 and a convex, posterior surface 184. Optic 180 includes a concave, anterior wall 186 and a convex, posterior wall 188.

The lens 170 of FIG. 15 is particularly unique in that each of the optics 178 and 180 of the combination optic 172 is prepared in a different state of accommodation. In the embodiment shown, optic 180 is formed in the disaccommodated state while the optic 178 is formed in the accommodated state. Due to strength differences, optic 180 has the greater influence when it is joined with optic 178. Thus, the overall combination optic 172 will rest in, or default to (absent a counteracting external force), the disaccommodated state due to the fact that optic 180 will stretch optic 178 to the disaccommodated state.

When the ciliary body (not shown) retracts or contracts as necessary (either pulling on the zonular fibers or releasing the pull on the zonular fibers), the fibrin (not shown) formed through openings 150 would result in a radially outward force on elements 176 (resulting in the thinning of optics 178, 180) or the release of that outward force (resulting in the thickening of optic 178, 180). Because optics 178, 180 are formed of materials (either the same or different) having respective refractive indices of greater than 1.33, thickening of optics 178, 180 would result in an increased convergence of light for near viewing, and thinning of optic 178, 180 would result in a decreased convergence of light for distance viewing.

Each of the foregoing embodiments can be used to obtain an accommodation improvement of at least about 1.5 diopters, preferably at least about 3.0 diopters, and more preferably from about 4-8 diopters. "Diopter" is defined as the reciprocal of the focal length in meters:

Diopter=1/focal length(m).

Focal length is the distance from the center of the lens to the object being viewed.

Importantly, this accommodation can be achieved with very little force being required by the eye. That is, the typical eye exerts anywhere from about 6-9 grams of force on an intraocular lens. However, the inventive optic can be designed to change shape sufficiently to produce the desired accommodation with as little as 1 gram of force. Thus, lenses according to the present invention provide a further advantage in that they can be designed to respond to a force over the entire range of from about 1 to about 9 grams.

For each of the foregoing embodiments illustrated in FIGS. 1-15, examples of suitable materials of which the lens and lens components (e.g., optic positioning elements, optics) can be constructed include any yieldable, synthetic resin material such as acrylates (e.g., polymethylmethacrylates), silicones, and mixtures of acrylates and silicones. It is particularly preferred that the optic positioning elements be constructed of a material having an elastic memory (i.e., the material should be capable of substantially recovering its original size and shape after a deforming force has been removed). An example of a preferred material having elastic memory is MEMORYLENS (available from Mentor Ophthalmics in California).

Furthermore, the optics of each embodiment could be formed of a wide range of flexible, refractive materials so long as the necessary thickening or thinning thereof can be achieved. Suitable materials include gels, silicone, silicone blends, refractive liquids, elastomeric materials, rubbers, acrylates, gases such as air, and mixtures of the foregoing, so long as the material is flexible and resilient. The shape of the optic (e.g., meniscus, biconcave, biconvex) utilized will depend upon the refractive index of the material used to form the optic. That is, the combination of optic shape and optic material will need to be chosen so that the resulting lens will converge light when the ciliary body contracts for near viewing.

While the foregoing description shows certain types of optic positioning elements with certain optics (both optic shapes and optic materials), it will be appreciated that this is for illustration purposes only, and the optic positioning elements and optic types can be switched. For example, the combination optic 172 of FIG. 15 could be utilized with the optic positioning element 33 of FIG. 1, the optic 32 of FIG. 1 could be utilized with the optic positioning element 144 of FIG. 12, etc.

Although the invention has been described with reference to the preferred embodiments illustrated in the attached drawing figures, it is noted that equivalents may be employed and substitutions made herein without departing from the scope of the invention as recited in the claims. For example, while the foregoing method of inserting the lens into the capsule presumed that a portion of the anterior wall of the capsule would be removed with the natural lens, it will be appreciated that it may be possible to insert the lens through an incision in the anterior wall. Furthermore, while the foregoing description discloses that the inventive lenses could be utilized in cataract patients, the lenses may be used in any situation where the natural lens needs to be replaced. For example, the inventive lenses may be used to correct myopia, hyperopia, presbyopia, cataracts, or a combination thereof.

Finally, it will be appreciated that each of the foregoing lenses can be manufactured in either the accommodated or disaccommodated shape. That is, they can be manufactured in a default state of either an accommodated or disaccommodated shape, and the deformed state (i.e., the state caused by the forces within the eye during focusing) will be the other of the accommodated or disaccommodated shape.

The invention claimed is:

1. An accommodating intraocular lens for implantation within an eye, comprising:
   a combination optic coupled to an optic positioning element, the combination optic comprising:
      a first optic comprising an anterior wall and a posterior wall;
      a second optic positioned anterior of the first optic and comprising a convex anterior surface and a convex posterior surface; and
      a first chamber that is sealed and is gas-filled, the first chamber being positioned between the anterior wall of the first optic and the convex posterior surface of the second optic,
   wherein the optic positioning element comprises an optic positioning wall and a bight, wherein the optic positioning wall extends from the combination optic, curves away from the combination optic to form the bight, and then continues curving until the optic positioning wall terminates at a location opposing the combination optic, wherein the optic positioning wall along with the combination optic form a second chamber with an opening allowing fluids to enter and fill the second chamber, and wherein the combination optic and the optic positioning element are configured to conform to the shape of a capsular bag.

2. The lens of claim 1, wherein at least one of the first and second optics is formed of a material selected from the group consisting of refractive solids, liquids and gels.

3. The lens of claim 1, wherein the optic positioning element is formed of a yieldable synthetic resin material.

4. The lens of claim 3, wherein the optic positioning element is formed of a material comprising a compound selected from the group consisting of silicone, polymethylmethacrylates, and mixtures thereof.

5. The lens of claim 1, wherein the first chamber has an initial thickness in the absence of an external force.

6. The lens of claim 5, wherein the intraocular lens is configured to decrease the initial thickness in response to ciliary body contraction.

7. The lens of claim 6, wherein the second optic has an initial thickness in the absence of an external force, the second optic being configured such that the initial thickness of the second optic increases to a second thickness in response to ciliary body contraction.

8. The lens of claim 5, wherein the intraocular lens is configured to alter the initial thickness in response to a change in force on the optic positioning element.

9. The lens of claim 1, wherein the anterior wall of the first optic is concave, and the posterior wall of the first optic is convex.

10. The lens of claim 1, wherein the second optic is positioned between the first chamber and the second chamber.

11. The lens of claim 1, wherein the first chamber spaces the anterior wall of the first optic from the convex posterior surface of the second optic.

12. The lens of claim 1, wherein the combination optic is positioned such that light passes through the opening, then through the second chamber, then through the second optic, then through the gas filling the first chamber, and then through the first optic to reach the retina of the eye.

13. The lens of claim 1, wherein the second optic is a solid optic.

14. The lens of claim 1, wherein the second optic is flexible.

15. The lens of claim 1, wherein the first chamber is configured to increase in thickness in response to ciliary body retraction.

16. The lens of claim 15, wherein the second optic is configured to decrease in thickness in response to ciliary body retraction.

* * * * *